United States Patent [19]

Piper

[11] 4,361,041
[45] Nov. 30, 1982

[54] NON-INTRUSIVE ULTRASONIC LIQUID-IN-LINE DETECTOR FOR SMALL DIAMETER TUBES

[75] Inventor: Thomas C. Piper, Idaho Falls, Id.

[73] Assignee: The United States of America as represented by the United States Department of Energy, Washington, D.C.

[21] Appl. No.: 190,303

[22] Filed: Sep. 24, 1980

[51] Int. Cl.³ .................................. G01N 29/02
[52] U.S. Cl. .............................. 73/579; 73/599
[58] Field of Search ............. 73/579, 592, 599, 290 V

[56] References Cited

U.S. PATENT DOCUMENTS 3,630,307 12/1971 Kamps et al. ...................... 73/599
3,744,301 7/1973 Arave ................................ 73/599
4,212,201 7/1980 Hirsch et al. ...................... 73/579

FOREIGN PATENT DOCUMENTS 1578660 11/1980 United Kingdom .

Primary Examiner—Anthony V. Ciarlante
Attorney, Agent, or Firm—Bruce R. Mansfield; Paul A. Gottlieb; Richard G. Besha

[57] ABSTRACT

An arrangement for deleting liquid in a line, using non-intrusive ultrasonic techniques is disclosed. In this arrangement, four piezoelectric crystals are arranged in pairs about a 0.072 inch o.d. pipe. An ultrasonic tone burst is transmitted along the pipe, between crystal pairs, and the amplitude of the received tone burst indicates the absence/presence of liquid in the pipe.

9 Claims, 4 Drawing Figures

NON-INTRUSIVE ULTRASONIC LIQUID-IN-LINE DETECTOR FOR SMALL DIAMETER TUBES

CONTRACTUAL ORIGIN OF THE INVENTION

The United States Government has rights in this invention pursuant to Contract No. DE-AC07-76IDO1540 between the U.S. Department of Energy and the Exxon Nuclear Idaho Company, Inc.

BACKGROUND OF THE INVENTION

Many industrial systems in operation today have lines or tubes designed to contain only air or other gases. Where a back-flow of liquids into these lines can create harmful conditions, or where such back-flow might indicate an unwanted diversion of expensive or dangerous liquids, means of detecting liquid would be useful. Also, where the lines contain radioactive materials or otherwise hostile environments, it is desirable to detect the presence of a liquid in a line without penetrating the line. Further difficulties are encountered in detecting liquids in small diameter tubes less than $\frac{3}{8}$ inches o.d., especially where the liquid backflow may contain entrapped gas.

Techniques for sensing fluid presence in a tube include measuring the conductivity or capacitance of a fluid, or measuring the attenuation of gamma, x-ray, visible or infra-red energy beams passed through a fluid. These techniques require costly equipment which is susceptable to damage, or misalignment, from rough handling. Further, these systems require continuous-wave excitation techniques, which are susceptible to deleterious reflection signals.

It is therefore an object of the present invention to detect the presence of liquid in a small diameter tube without penetrating the tube.

Another object of the present invention is to detect the presence of liquid in a tube without using continuous-wave excitation techniques.

An additional object of the invention is to provide an accurate and reliable liquid detection scheme that may be embodied in durable, relatively inexpensive equipment.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

These and other objects of the present invention are accomplished by providing an arrangement for detecting the presence of liquids in a line, by measuring the liquid-induced change in an ultrasonic signal which is coupled to the line.

Non-intrusive ultrasonic liquid-in-line sensors of the electrical-mechanical transducing type are secured to the outside of the line to be monitored. Short bursts of an ultrasonic signal are transmitted between transducing elements. The first few cycles received are isolated and their amplitude is measured. A reduced amplitude indicates the presence of a liquid in the line. Two transducer arrangements are provided for lines of varying sizes. A first arrangement comprises longitudinally displaced transducing elements bonded to a flat region formed along the outer surface of the line. Another arrangement, especially suited for very small size lines, comprise pairs of sending and receiving transducers bonded to the outside surface of a line. No flats are formed in the line of the second embodiment. The sending transducers are diametrically opposed to each other, as are the pair of receiving transducers. The receiving transducers are rotated 90° with respect to the pair of sending transducers and are axially displaced therefrom. In either arrangement, the tubing walls are operated in a flexural mode, wherein the wall of the line flexes in resonance in response to longitudinal excitation of the drive transducers.

DESCRIPTION OF THE PREFERRED EMBODIMENT

Figure 1:
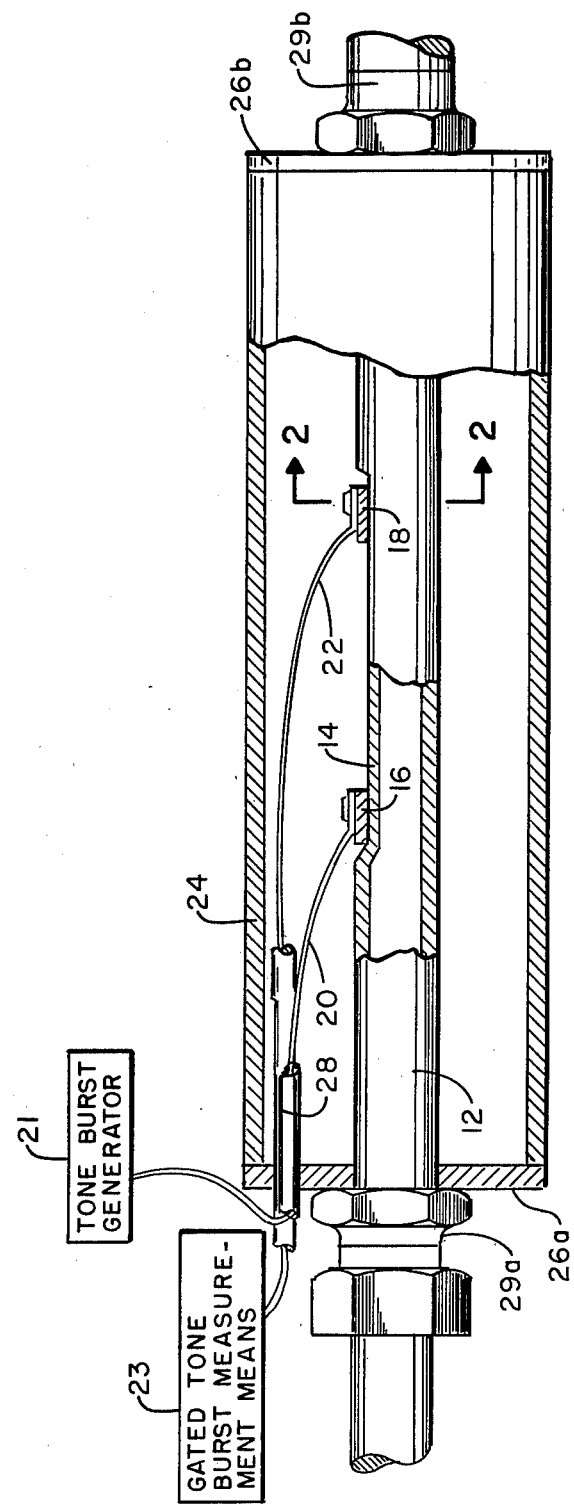
FIG. 1 shows a first embodiment of a detector according to the invention.
Figure 2:
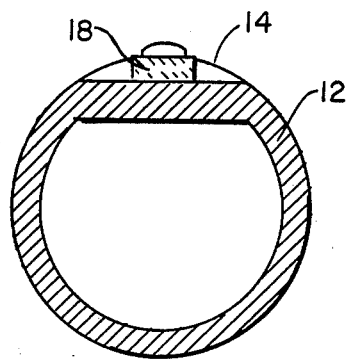
FIG. 2 shows a sectional view, taken along the lines 2—2 of FIG. 1.

Referring now to the drawings, and in particular to FIGS. 1 and 2, a first embodiment of a non-intrusive ultrasonic liquid-in-line detector 10 is shown. Detector 10 comprises a metallic conduit or tubing 12. A flattened region 14 is formed in tubing 12 with an internal mandrel or may be formed by any other suitable method. Sender and receiver transducers 16, 18 respectively, are mechanically and electrically bonded to the flattened region 14 of tubing 12 in axially displaced relationship, such that there is no rotational displacement therebetween. Electrical lead 20 connects transducer 16 to a tone burst generator 21. Electrical lead 22 connects transducer 18 to an electrical circuit 23 which measures the amplitude of the tone burst response of transducer 18, and gates the output of the transducer in a prescribed fashion, as will be explained hereafter. Either transducer 16, 18 can act as a sender or receiver transducer. When an ultrasonic signal passes between transducers 16, 18, the flattened region 14 vibrates with undulatory motion. The ultrasonic signal is a series of tone bursts, with the times between the bursts sufficiently long so as to allow various deflections of the tone bursts to decay away. Thus, the arrangement of the present invention overcomes the disadvantages of continuous-wave methods which are hampered by spurious reflections of the transmitted beam along the path between the drive and receive transducers. The system also overcomes disadvantages of through transmission, shear wave, and torsional wave modes of detection. By using the toneburst method of detection of the present invention, a clear difference in liquid-absent and liquid-present signals is distinguishable. Further, the method of the present invention is fail-safe, does not require accurate time measurement equipment, and allows accurate control of transmitted signals between drive and receive transducers.

A working model of the above arrangement consisted of two PZT5A piezoelectric crystals, 0.035 inches thick, 0.05 inches wide, and 0.12 inches long. The crystals were of the "3,3" compression mode polarization type and were bonded to a $1\frac{1}{2}$ inch long flattened region of a $\frac{1}{4}$ inch diameter stainless steel tube. The tube had a wall thickness of 0.035 inches. The flattened region was approximately 0.12 inches wide and was formed by squeezing the tube after an appropriately sized mandrel was inserted therein. The crystals are positioned adjacent each end of the flattened region, such that they were separated by a distance of approximately ⅞ inches. The crystals were mounted such that their 0.05 inch width was arranged parallel to the longitudinal axis of the tube. Either crystal could function as the drive or receiver transducer. For each crystal, the crystal surface bonded to the tube was one of the two electroded surfaces of the crystal which were positioned normal to the crystal 3,3 direction. The bonding of the first crystal electrode surface formed an electrical connection between the crystal and the tube. The second electrode of each crystal is electrically connected to associated circuitry. The driver crystal was excited at about 480 kilohertz, which set the flattened region into an undulatory motion. Since the rest of the tube acted to stiffen this flattened portion, the natural resonance frequency thereof was considerably higher than it would be if it were unattached to the remainder of the tube. Because much of the tubing wall vibrated, the rather high impedance of the driving piezoelectric crystal became fairly well matched to that of any liquid which may have been present in the tube, with energy of the vibration being coupled into that liquid and being dissipated. When the sensing portion of the tube contained only air, the tube wall undulation was only slightly damped and most of the vibration reached the receiving crystal, giving a significant output.

The natural resonance frequency of a flattened tube will change, because Young's modulus for stainless steel tubing is a function of temperature. However, the most pronounced temperature effect arises from changes in reflections within the tubing walls, but by driving the sensor with eight cycles of a 480 kilohertz tone burst (i.e. 16.7 microsecond duration) at a one kilohertz repetition rate, no reflections are present with the first portion, i.e., the first few cycles, of the received signal. Therefore, temperature effects do not require changes in operating frequency. Also, the "liquid-absent" output amplitude remains nearly constant throughout the temperature cycle. In situations where a "liquid-absent" condition is the usual or "safe" condition, the unit is "fail-safe" in that its most likely failure modes will signal the presence of liquid rather than give no alarm at all that the detector has failed. The signal at the receive crystal begins about 6 microseconds after the drive tone burst is initiated, and the receive signal begins to decay when the tone burst is over. The signal from the receiver is gated "on" during this 16.7 microsecond time segment. After the primary response to the tone burst is over, the output from the receive crystal although not gated through any longer, continues to respond to various reflections of the signal as it decays away. The output is substantially terminated after approximately 150 microseconds, assuming the received tone burst is gated on for only eight cycles of the 480 kilohertz signal. Therefore, successful operation of the detector arises from gating the received signal so as to monitor no more than the first eight cycles of signal arriving at the received crystal.

FIGS. 1 and 2 show a ruggedized detector completely encapsulated in an outer stainless steel sleeve 24 which is welded onto washer-like end walls 26a, 26b. Electrical leads 20, 22 pass through an aperture 28 formed in end wall 26a. Quick-disconnect fittings 29a, 29b are also provided to permit ready insertion into a line of an external system to be monitored.

Although the above model utilized a stainless steel tubing having a ¼ inch diameter and a wall thickness of 0.035 inches, the arrangement shown above can be incorporated in metallic tubing having outside diameters ranging from 0.375 to 0.20 inches and having wall thickness ranging from 0.035 to 0.025 inches. In general, as the tubing outside diameter is decreased, or as the tubing wall thickness is increased, the excitation frequency of the drive crystal must be decreased. The 480 kilohertz frequency signal can be varied from 480 to 630 kilohertz for the ¼ inch tubing described above, and different frequency ranges must be provided to accommodate different tubing sizes. In each case, however, the piezoelectric crystal thickness must be selected to provide loaded resonance frequencies above the tubing materials undulatory frequency.

Figure 3:
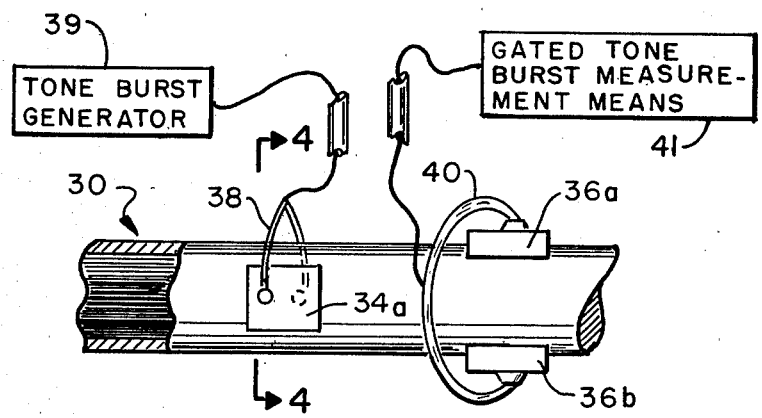
FIG. 3 shows a second embodiment of a detector according to the invention.
Figure 4:
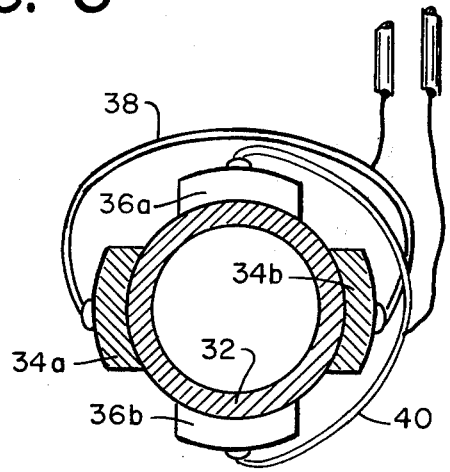
FIG. 4 shows a sectional view, taken along the line 4—4 of FIG. 3.

Referring now to FIGS. 3 and 4, a second embodiment of the detector suitable for smaller size lines, is described. The non-intrusive ultrasonic liquid-in-line detector 30 is shown comprising a metallic conduit or tubing 32. A pair of drive crystals, 34a, 34b are bonded to the tubing 32 in diametrically opposed relationship. A pair of receive crystals, 36a, 36b are bonded to tubing 32 in diametrically opposed relationship, such that they are rotated 90° with respect to drive crystals 34a, 34b, and are axially displaced therefrom. Drive transducers 34a, 34b are electrically connected together by an electrical lead 38 which is in turn connected to an external tone burst generator 39. The tubing serves as the other lead to complete the electrical circuit. Similarly, receive transducers 36a, 36b are electrically connected together by lead 40 which is in turn connected to an electronic circuit 41 which measures the amplitude of the received tone burst and gates the output of transducers 36a, 36b in a prescribed fashion as will be explained hereafter. Either diametrically opposed pair of crystals may function as the drive or receiver transducers. When an ultrasonic signal passes between drive transducers 34a, 34b and receive transducers 36a, 36b, tubing 32 vibrates with an undulatory (inward and outward flexural) motion. The ultrasonic signal applied to the drive transducers comprises a series of tone bursts, with the times between the tone bursts sufficiently long so as to allow various reflections of the tone bursts to decay away. Thus, the second embodiment overcomes the disadvantages of continuous wave methods as well as through transmission, shear wave, and tortional wave modes of detection described above.

A working model of the above detector arrangement was constructed and operated. The detector was comprised of four PZT5A piezoelectric crystals with "3,3" compression mode polarization, bonded to a 0.072 inch O.D., hypodermic type stainless steel tube having a 0.009 inch wall thickness. Each crystal has dimensions of 0.01 inch thickness, 0.032 inch width, and 0.05 inch length. The crystals are mounted such that the edge of 0.05 inch length is arranged parallel to the axis of the tube. For each crystal, the crystal surface bonded to the tube is one of the two electroded surfaces of the crystal which are positioned normal to the crystal 3,3 direction. The bonding of the first crystal electrode surface of each crystal forms an electrical connection between the crystal and the tube. For each pair of drive crystals and for each pair of receive crystals, each crystal of the pair has the same crystal polarity face bonded and electrically connected to the tubing 32. No flats are put on the tubing, as were required in the first embodiment. The axial displacement between the drive crystal pair and the receive crystal pair is 0.1 inches. Because the drive crystals are connected electrically in parallel and have the same polarity, drive crystal electrical excitation causes an inward and outward flexure of the tubing. At an excitation resonance frequency of 2.154 megahertz, there is adequate tubing wall flexure for the parallel-connected receiver crystals to sense the wall vibration.

The output amplitude from this configuration provided a reliable response over wide temperature range. Sixteen cycles of the 2.154 megahertz drive signal, at three volts rms, produced a "liquid-absent" output of 70 millivolts (zero-to-peak) and a "liquid-present" output of 23 millivolts (zero-to-peak). These amplitudes are constant to about ±3 millivolts for temperatures up to 70° centigrade. Again, the receiver signal is gated "on" so as to monitor a burst of the first 16 cycles of received signal, which corresponds to the 16 cycle burst of excitation signal applied to the drive pair of crystals. Thus, the deleterious effects of unwanted reflected signals is avoided.

While the tubing of the model described above had an outside diameter and wall thickness of 0.072 inches and 0.009 inches respectively, the outside diameter can range from 0.06 to 0.2 inches. A higher excitation frequency must, in general, be provided for smaller conduit outside diameters and larger conduit wall thickness. Crystal thickness must be adjusted so as to provide loaded resonance frequencies above the tubing material's undulatory frequency.

The embodiments of this invention in which an exclusive property or privilege is claimed are defined as follows:

1. A means for detecting liquid in a conduit comprising:
   at least one driving transducer electrically and mechanically connected to a first portion of an outside surface of the conduit;
   at least one receiving transducer electrically and mechanically connected to a second spaced apart portion of an outside surface of the conduit;
   means for exciting said drive transducer with an ultrasonic tone burst such that said conduit vibrates in an undulatory motion, said tone burst being transmitted to said receiver transducer; and
   means for measuring the amplitude of said tone burst at an output of said receiver transducer while excluding responses of said receiver transducer after said tone burst is received, whereby the presence of a liquid in said conduit is detected.

2. The apparatus of claim 1, wherein a flattened region is formed on the outside surface of said conduit and said first and said second portions of said conduit are contained in said flattened region.

3. The apparatus of claim 1, wherein said conduit has a longitudinal axis, said driver and said receiver transducers being aligned in longitudinally spaced-apart relationship.

4. The apparatus of claim 3, wherein said transducers are piezoelectric crystals of the 3,3 compression mode polarization type.

5. The apparatus of claim 1, wherein another drive transducer is mechanically and electrically bonded to an outside surface of said conduit in diametrically opposed relationship to said one drive transducer.

6. The apparatus of claim 1 wherein another receiver transducer is mechanically and electrically bonded to an outside surface of said conduit in diametrically opposed relationship to said one receiver transducer, such that said one and said other receiver transducers are displaced 90° from, and are longitudinally spaced-apart from one and said other drive transducers;
   said one and said other drive transducers are electrically connected together and to said means for exciting; and
   said one and said other receiver transducers are electrically connected together and to said means for measuring.

7. The apparatus of claim 6, wherein said one and said other transducers are piezoelectric crystals having crystal faces of the same polarity bonded to said conduit.

8. The apparatus of claim 7, wherein the outside diameter of said tubing is less than 0.2 inches.

9. The apparatus of claim 8, wherein the outside diameter of said tubing is less than 3/8 inches.

* * * * *